US012662398B2

(12) United States Patent
Miyajima

(10) Patent No.: US 12,662,398 B2
(45) Date of Patent: Jun. 23, 2026

(54) ULTRAVIOLET LIGHT FLUID TREATMENT DEVICE

(71) Applicant: NICHIA CORPORATION, Anan (JP)

(72) Inventor: Shunsuke Miyajima, Suwa (JP)

(73) Assignee: NICHIA CORPORATION, Anan (JP)

( * ) Notice: Subject to any disclaimer, the term of this patent is extended or adjusted under 35 U.S.C. 154(b) by 361 days.

(21) Appl. No.: 18/491,046

(22) Filed: Oct. 20, 2023

(65) Prior Publication Data

US 2024/0150201 A1 May 9, 2024

(30) Foreign Application Priority Data

Nov. 7, 2022 (JP) ................................. 2022-178450

(51) Int. Cl.
C02F 1/32 (2023.01)
A61L 9/20 (2006.01)
(52) U.S. Cl.
CPC ................ C02F 1/325 (2013.01); A61L 9/20 (2013.01); *A61L 2209/12* (2013.01); *C02F 2201/3228* (2013.01); *C02F 2303/04* (2013.01)
(58) Field of Classification Search
CPC .............. C02F 1/325; C02F 2201/3222; C02F 2303/04; C02F 1/32; A61L 2/10
See application file for complete search history.

(56) References Cited

U.S. PATENT DOCUMENTS 6,419,821 B1 * 7/2002 Gadgil ............... B01D 39/2068
210/256
8,872,130 B1 * 10/2014 Matthews ............... C02F 1/325
210/764

11,092,977 B1 * 8/2021 Coleman .................. G02B 3/12
11,525,566 B1 * 12/2022 Shiraishi ................. F21V 23/06
2005/0194896 A1 * 9/2005 Sugita .................... B82Y 30/00
313/506
2007/0102280 A1 * 5/2007 Hunter ................. B01D 53/007
422/186.3
2007/0108056 A1 * 5/2007 Nyberg .................. B01D 61/54
204/554
2009/0250407 A1 * 10/2009 Delano ............... B01F 23/2341
210/241

(Continued)

FOREIGN PATENT DOCUMENTS

JP 2000206912 A 7/2000
JP 2006310632 A 11/2006

(Continued)

*Primary Examiner* — Wyatt A Stoffa

*Assistant Examiner* — Jing Wang

(74) *Attorney, Agent, or Firm* — Hunton Andrews Kurth LLP

(57) ABSTRACT

An ultraviolet light fluid treatment device for irradiating a fluid flowing in a flow path tube with ultraviolet light includes a substrate; a light source disposed on the substrate and configured to emit the ultraviolet light; a light transmissive member disposed between the light source and the flow path tube and configured to transmit the ultraviolet light from the light source; and a support member fixed to the substrate and configured to hold an adsorption member that includes an adsorbent material adsorbing moisture. The support member has a reflective surface. The reflective surface is positioned between the light source and the adsorption member, and is configured to reflect the ultraviolet light from the light source.

19 Claims, 6 Drawing Sheets

(56)          References Cited

U.S. PATENT DOCUMENTS

| | | | | |
|---|---|---|---|---|
| 2010/0000874 A1* | 1/2010 | Hinman | .................. | F24S 23/74 |
| | | | | 205/340 |
| 2012/0138545 A1* | 6/2012 | Soler | ........................ | C02F 1/30 |
| | | | | 422/186.3 |
| 2013/0092969 A1 | 4/2013 | Hikmet et al. | | |
| 2015/0035437 A1* | 2/2015 | Panopoulos | ............ | B60L 53/12 |
| | | | | 315/291 |
| 2015/0284266 A1* | 10/2015 | Matsui | .................... | C02F 1/325 |
| | | | | 422/24 |
| 2018/0086649 A1* | 3/2018 | Hayashi | .................. | C02F 1/325 |
| 2019/0054201 A1* | 2/2019 | Zhang | ....................... | A61L 9/20 |
| 2019/0135658 A1* | 5/2019 | Yamakoshi | ........... | B08B 7/0057 |
| 2020/0283311 A1* | 9/2020 | Wong | ....................... | C02F 1/325 |
| 2020/0331775 A1* | 10/2020 | Schowalter | ............... | A61L 2/10 |
| 2021/0087078 A1* | 3/2021 | Schowalter | ............. | C02F 1/325 |
| 2021/0260228 A1* | 8/2021 | Wong | ....................... | A23B 2/53 |
| 2021/0300792 A1* | 9/2021 | Barnes | .................... | C02F 1/325 |
| 2022/0098058 A1* | 3/2022 | Kato | ........................ | C02F 1/325 |
| 2022/0324727 A1* | 10/2022 | Magg | ....................... | C02F 1/325 |
| 2022/0331465 A1* | 10/2022 | Childress | .................. | A61L 2/10 |
| 2022/0362431 A1* | 11/2022 | Efrati | ......................... | A61L 9/20 |
| 2022/0363568 A1* | 11/2022 | Kung | ....................... | C02F 1/001 |
| 2026/0063966 A1* | 3/2026 | Tan | ........................ | G02F 1/3515 |

FOREIGN PATENT DOCUMENTS

| | | | |
|---|---|---|---|
| JP | 2011054529 A | 3/2011 | |
| JP | 2013536569 A | 9/2013 | |
| JP | 2019021463 A | 2/2019 | |
| JP | 2020044301 A | 3/2020 | |
| JP | 2022055050 A | 4/2022 | |

* cited by examiner

ULTRAVIOLET LIGHT FLUID TREATMENT DEVICE

CROSS-REFERENCE TO RELATED APPLICATIONS

This application is based on and claims priority to Japanese Patent Application No. 2022-178450, filed on Nov. 7, 2022, the entire contents of which are incorporated herein by reference.

FIELD

The disclosure herein relates to an ultraviolet light fluid treatment device.

BACKGROUND

JP-A 2011-054529 describes an ultraviolet light fluid treatment device that includes a light emitting element, such as a light emitting diode (LED), and a secondary reflector, and further includes a moisture absorbent such that a space in which the light emitting element is housed is maintained in a dry state.

SUMMARY

According to the present disclosure, it is desirable to provide a small-sized ultraviolet light fluid treatment device that can adsorb moisture around a light source.

According to an embodiment of the present disclosure, an ultraviolet light fluid treatment device for irradiating a fluid flowing in a flow path tube with ultraviolet light includes a substrate; a light source disposed on the substrate and configured to emit the ultraviolet light; a light transmissive member disposed between the light source and the flow path tube and configured to transmit the ultraviolet light from the light source; and a support member fixed to the substrate and configured to hold an adsorption member that includes an adsorbent material adsorbing moisture. The support member has a reflective surface. The reflective surface is positioned between the light source and the adsorption member, and is configured to reflect the ultraviolet light from the light source to the light transmissive member.

BRIEF DESCRIPTION OF THE DRAWINGS

Other objects and further features of the present invention will be apparent from the following detailed description when read in conjunction with the accompanying drawings, in which.

DETAILED DESCRIPTION

Figure 1:
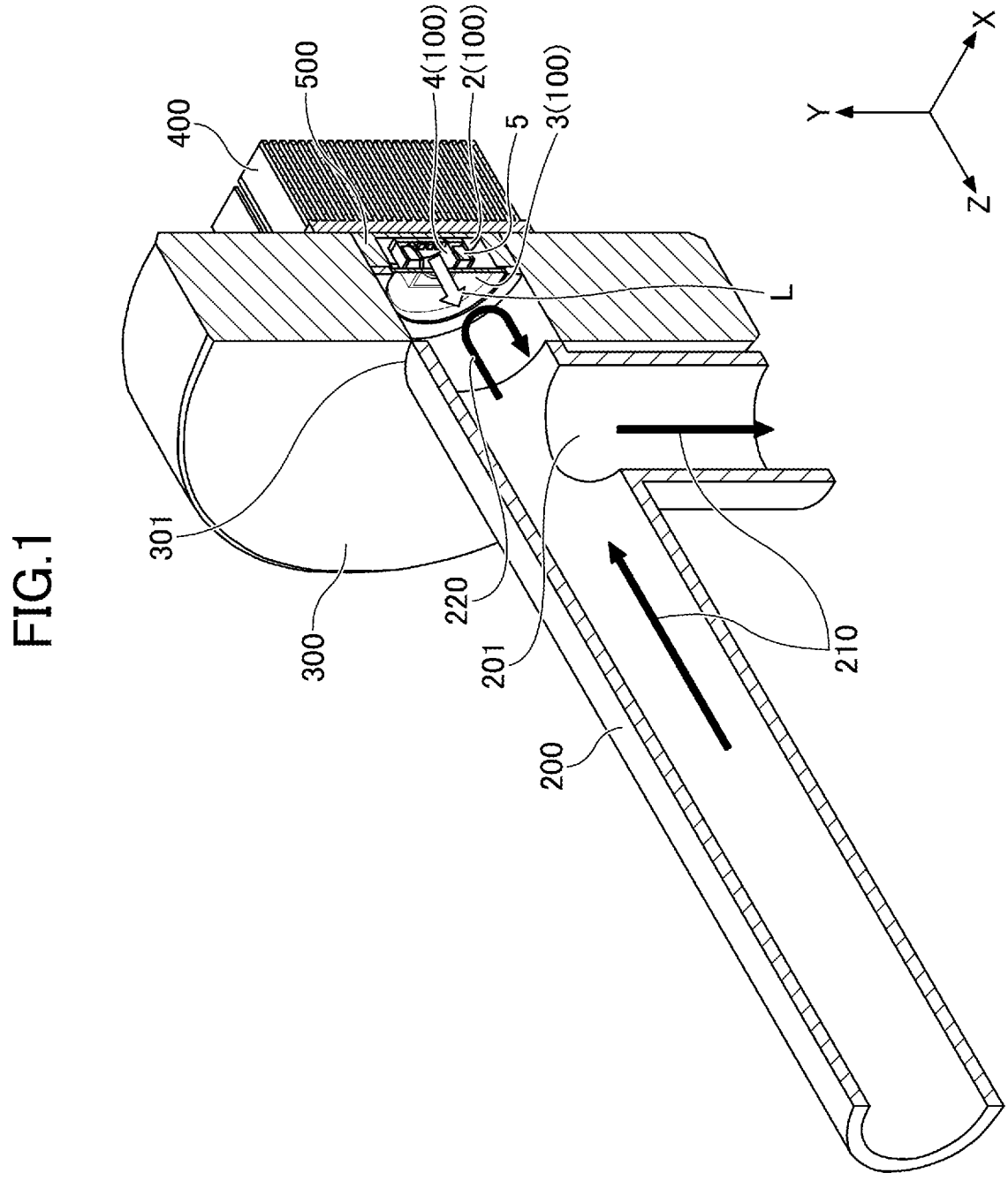
FIG. 1 is a schematic cross-sectional perspective view of an ultraviolet light fluid treatment device according to an embodiment, which is configured to irradiate a fluid in a flow path tube with ultraviolet light.

In the following, an ultraviolet light fluid treatment device according to embodiments of the present disclosure will be described in detail with reference to the accompanying drawings. The following embodiments exemplify the ultraviolet light fluid treatment device to embody the technical idea of the embodiment, and are not limited to the following description. In addition, unless otherwise specified, the dimensions, materials, shapes, relative arrangements, and the like of components described in the embodiments are not intended to limit the scope of the present disclosure thereto, but are described as examples. The sizes, positional relationships, and the like of members illustrated in the drawings may be exaggerated for clearer illustration. Further, in the following description, the same names and reference numerals denote the same or similar members, and a detailed description thereof will be omitted as appropriate. An end view illustrating only a cut surface may be used as a cross-sectional view.

In the drawings, in order to indicate directions, an orthogonal coordinate system having an X-axis, a Y-axis, and a Z-axis is used. The X-axis, the Y-axis, and the Z-axis are orthogonal to one another. In the present specification, an axis along a direction normal to a main surface of a light transmissive member of the ultraviolet light fluid treatment device according to the embodiments is the Z-axis. The direction normal to the main surface of the light transmissive member is orthogonal to a light emitting surface of a light source of the ultraviolet light fluid treatment device according to the embodiments. Axes orthogonal to the direction normal to the main surface of the light transmissive member are the X-axis and the Y-axis.

A direction indicated by an arrow in the X direction along the X-axis is referred to as a +X direction or a +X side, and a direction opposite to the +X direction is referred to as a −X direction or a −X side. A direction indicated by an arrow in the Y direction along the Y-axis is referred to as a +Y direction or a +Y side, and a direction opposite to the +Y direction is referred to as a −Y direction or a −Y side. A direction indicated by an arrow in the Z direction along the Z-axis is referred to as a +Z direction or a +Z side, and a direction opposite to the +Z direction is referred to as a −Z direction or a −Z side. However, these directions are not intended to limit the directions of the ultraviolet light fluid treatment device according to the embodiments of the present invention.

In the present specification and the claims, the expression "in a plan view" refers to viewing an object from the Z direction, that is, from the direction normal to the main surface of the light transmissive member of the ultraviolet light fluid treatment device according to the embodiments. Further, in the present specification and the claims, the +Z direction or the +Z side is referred to as an "upper side", the −Z direction or the −Z side is referred to as a "lower side", and the end in the +Z direction or on the +Z side is referred to as an "upper end". Further, in the present specification, each of "along the X-axis", "along the Y-axis", and "along the Z-axis" includes a case where the object is at an inclination within a range of ±10° with respect to the corresponding one of the axes. Further, the term "orthogonal" may include an error within ±10° with respect to 90°.

<Example of Overall Configuration of Ultraviolet Light Fluid Treatment Device 100>

Figure 2:
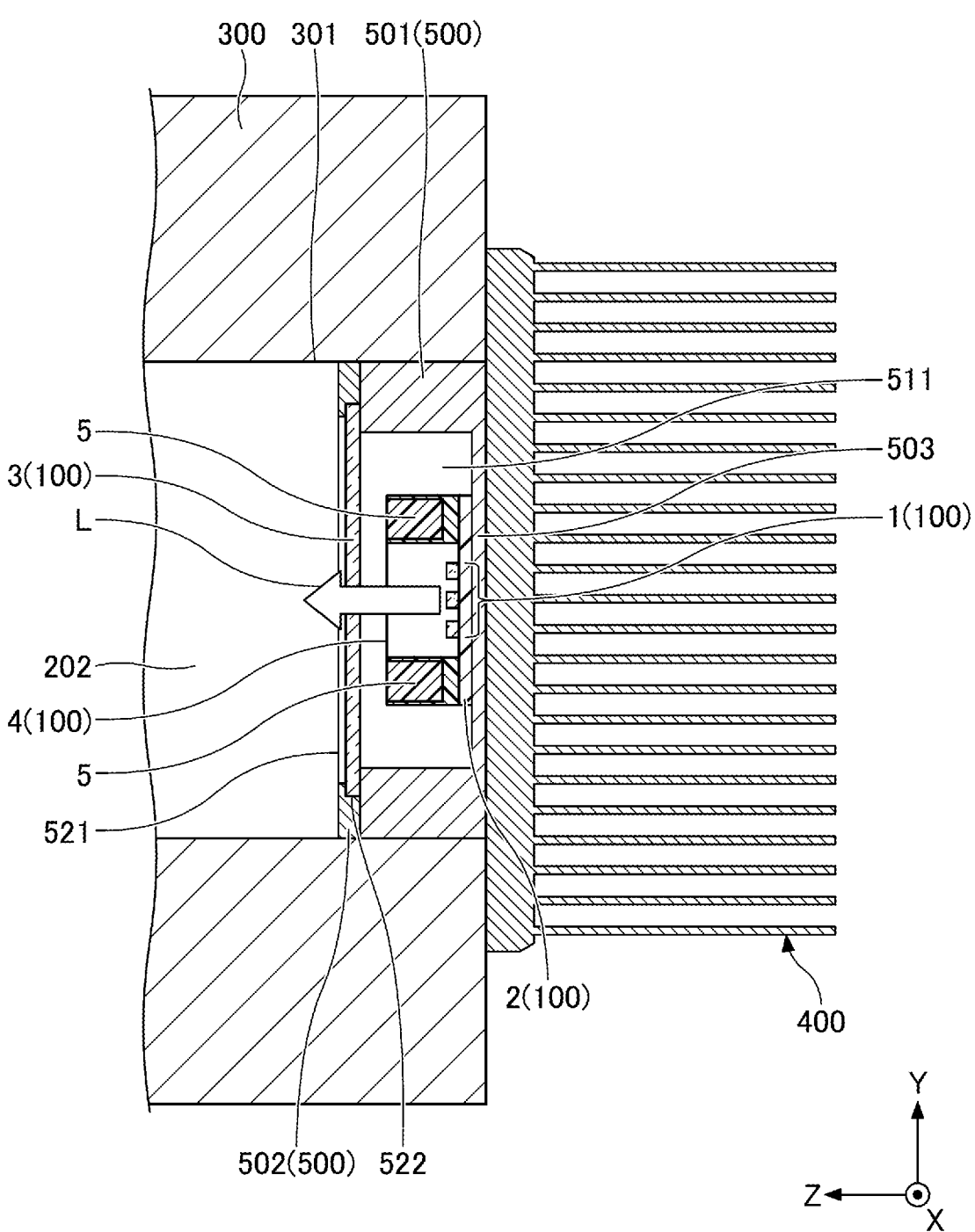
FIG. 2 is a schematic cross-sectional view of the vicinity of the ultraviolet light fluid treatment device of FIG. 1.
Figure 3:
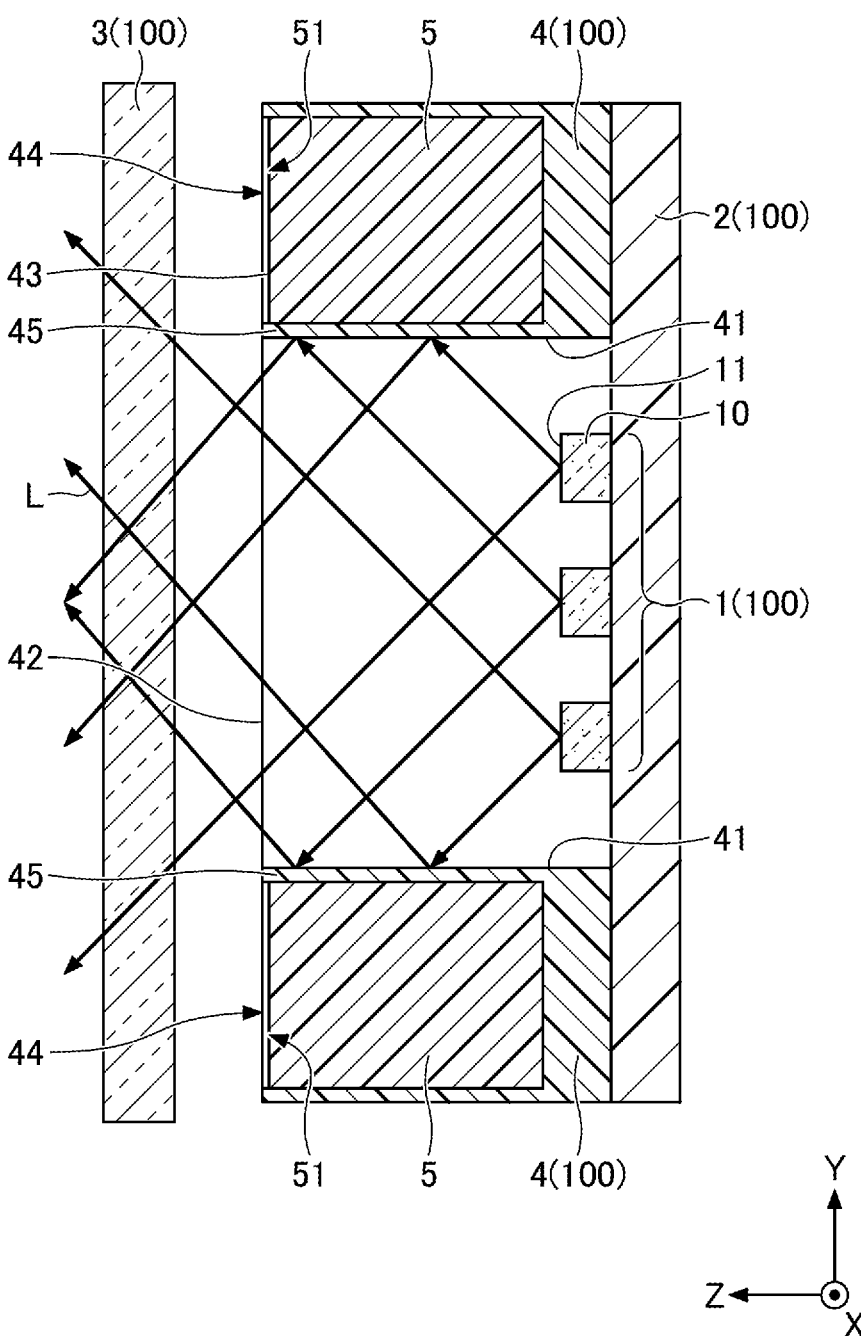
FIG. 3 is a schematic enlarged cross-sectional view of the ultraviolet light fluid treatment device of FIG. 1.

The overall configuration of an ultraviolet light fluid treatment device 100 according to an embodiment will be described with reference to FIG. 1 through FIG. 3. FIG. 1 is a schematic cross-sectional perspective view of the ultraviolet light fluid treatment device 100 configured to irradiate a fluid in a flow path tube 200 with ultraviolet light. FIG. 2 is a schematic cross-sectional view of the vicinity of the ultraviolet light fluid treatment device 100 of FIG. 1. FIG. 3 is a schematic enlarged cross-sectional view of the ultraviolet light fluid treatment device 100 of FIG. 1. The cross sections in FIG. 1 through FIG. 3 are parallel to the Y-axis and the Z-axis and are orthogonal to the X-axis.

The ultraviolet light fluid treatment device 100 is a device configured to irradiate a fluid flowing in the flow path tube with ultraviolet light. The examples of the fluid include a liquid, a gas, and the like. As illustrated in FIG. 1 through FIG. 3, the ultraviolet light fluid treatment device 100 can treat a fluid flowing in the flow path tube 200 by irradiating the fluid with ultraviolet light L. For example, water can be treated by being irradiated with the ultraviolet light L so as to reduce the number of bacteria and viruses in the water after the treatment as compared to before the treatment.

The ultraviolet light fluid treatment device 100 includes a light source 1, a substrate 2, a light transmissive member 3, and a support member 4. The light source 1 is disposed on the substrate 2, and is configured to emit the ultraviolet light L. The light transmissive member 3 is disposed between the light source 1 and the flow path tube 200, and is configured to transmit the ultraviolet light L from the light source 1. The support member 4 is fixed to the substrate 2, and is configured to hold an adsorption member 5 that includes an adsorbent material adsorbing moisture.

The light transmissive member 3 functions as a window part that transmits the ultraviolet light L from the light source 1 to the outside of the ultraviolet light fluid treatment device 100. The light transmissive member 3 preferably transmits 80% or more of the ultraviolet light L from the light source 1. The light transmissive member 3 has a substantially circular outer shape in a plan view. However, the light transmissive member 3 may have a shape other than the substantially circular shape, such as a substantially elliptical shape, a substantially rectangular shape, or a substantially polygonal shape in a plan view. Examples of a material included in the light transmissive member 3 include inorganic materials formed of at least one selected from the group consisting of quartz glass, borosilicate glass, calcium fluoride glass, aluminoborosilicate glass, oxynitride glass, chalcogenide glass, and sapphire.

As illustrated in FIG. 1 and FIG. 2, the ultraviolet light fluid treatment device 100 and the flow path tube 200 are fixed to a flange 300. The flange 300 has a through hole 301 penetrating the flange 300 in the Z direction. The opening of the through hole 301 has a substantially circular shape in a plan view. However, the through hole 301 may have a shape other than the substantially circular shape, such as a substantially elliptical shape, a substantially rectangular shape, or a substantially polygonal shape in a plan view.

The flow path tube 200 is a tubular member in which a fluid flows. The flow path tube 200 is fixed to the flange 300 such that the fluid flowing in the flow path tube 200 can enter the through hole 301. In FIG. 1, flows 210 indicated by arrows represent the flows of the fluid in the flow path tube 200. A flow 220 indicated by an arrow represents the flow of the fluid entering the through hole 301 from the flow path tube 200.

In the example illustrated in FIG. 1, after the fluid in the flow path tube 200 flows in the −Z direction, a portion of the fluid flows in the −Y direction at a branch portion 201, and the other portion of the fluid enters the through hole 301 toward the light transmissive member 3. The flow 220 is caused by the portion of the fluid that enters the through hole 301 and remains in the vicinity of the light transmissive member 3 by hitting and bouncing back from the light transmissive member 3. After remaining in the vicinity of the light transmissive member 3, the portion of the fluid flows in the +Z direction, and then flows in the −Y direction at the branch portion 201. The shape of the flow path tube 200, the flow directions of the fluid, and the like are not limited to those illustrated in FIG. 1, and can be appropriately changed according to the application or the like of the ultraviolet light fluid treatment device 100.

The ultraviolet light fluid treatment device 100 is fixed to a heat sink 400 via an attachment member 500. The attachment member 500 to which the ultraviolet light fluid treatment device 100 is attached is inserted into the through hole 301 from the side of the flange 300 opposite the flow path tube 200, and in this state, the heat sink 400 is fixed to the flange 300 by using a screw member, an adhesive member, or the like. By fixing the heat sink 400 to the flange 300, the ultraviolet light fluid treatment device 100 is disposed to face the fluid flowing in the flow path tube 200 along the Z direction.

With the attachment member 500 being fixed to the flange 300, a gap between the attachment member 500 disposed within the through hole 301 and the inner surface defining the through hole 301 is preferably sealed by a sealing member or the like. By sealing the gap, the fluid entering the through hole 301 from the flow path tube 200 can be reduce from leaking to the outside of the flange 300 through the gap.

The heat sink 400 is configured to include a material having high thermal conductivity such as aluminum. The heat sink 400 can dissipate heat generated by the light source 1 accompanying light emission or the like and conducted through the attachment member 500.

As illustrated in FIG. 2, the attachment member 500 includes a body 501 and a cover 502. The attachment member 500 has a substantially circular outer shape in a plan view. However, the attachment member 500 may have an outer shape other than the substantially circular shape, such as a substantially elliptical shape, a substantially rectangular shape, or a substantially polygonal shape in a plan view. The attachment member 500 is configured to include a metal material, a resin material, or the like.

The body 501 includes a recessed portion 511. The recessed portion 511 has a substantially circular shape in a plan view. The cover 502 is an annular member that has an opening 521 having a substantially circular shape in a plan view, and includes a holding portion 522. The holding portion 522 is a recessed portion formed along the edge of the opening 521. The holding portion 522 can hold the light transmissive member 3 by fitting the light transmissive member 3 to the holding portion 522. The light transmissive member 3 can be fixed to the holding portion 522 by using an adhesive member or the like. Each of the recessed portion 511 and the opening 521 may have a shape other than the substantially circular shape, such as a substantially elliptical shape, a substantially rectangular shape, or a substantially polygonal shape.

In a state in which the surface (on the −Z side) of the substrate 2 opposite the surface (on the +Z side) on which the light source 1 is disposed contacts the surface on the +Z side of a bottom portion 503 of the recessed portion 511 of the attachment member 500, the substrate 2 is fixed to the bottom portion 503 of the recessed portion 511 by using an adhesive member or the like. In a state in which the light transmissive member 3 is held by the holding portion 522, the cover 502 is placed on the surface on the +Z side of the body 501 of the attachment member 500, and is fixed to the body 501 by using a screw member, an adhesive member, or the like. The substrate 2 has a substantially rectangular outer shape in a plan view. The outer shape of the substrate 2 can be, for example, a square having each side of 1 cm or more and 3 cm or less.

By disposing the attachment member 500 in the through hole 301, the light transmissive member 3 is disposed between the flow path tube 200 and the light source 1 while closing the opening of the recessed portion 511. With this configuration, the ultraviolet light fluid treatment device 100 can cause the ultraviolet light L from the light source 1 to be transmitted through the light transmissive member 3, and can irradiate a fluid 202 flowing in the flow path tube 200 with the ultraviolet light L. Further, by disposing the light transmissive member 3 between the flow path tube 200 and the light source 1, the ultraviolet light fluid treatment device 100 can reduce the fluid 202 flowing in the flow path tube 200 from entering the recessed portion 511 of the attachment member 500. Accordingly, if the fluid 202 is a liquid, the ultraviolet light fluid treatment device 100 can reduce the fluid 202 from wetting the light source 1, the substrate 2, the support member 4, and the like.

With the cover 502 being fixed to the body 501, a gap between the upper surface (on the +Z side) of the body 501 and the lower surface (on the −Z side) of the cover 502 is preferably sealed by a sealing member or the like. Further, with the light transmissive member 3 being held by the holding portion 522 of the cover 502, a gap between the cover 502 and the light transmissive member 3 is preferably sealed by a sealing member or the like. By sealing these gaps, the ultraviolet light fluid treatment device 100 can reduce the fluid 202 from entering the recessed portion 511 of the attachment member 500.

As illustrated in FIG. 3, the light source 1 includes a plurality of light emitting parts 10. The light emitting parts 10 include respective light emitting surfaces 11. The light source 1 emits the ultraviolet light L mainly from the light emitting surfaces 11 of the plurality of light emitting parts 10. Each of the light emitting parts 10 has a substantially rectangular outer shape in a plan view. The outer shape of each of the light emitting parts 10 can be, for example, a square having each side of 0.1 cm or more and 0.2 cm or less.

The support member 4 includes a reflective surface 41, a through hole 42, and recessed portions 43. The support member 4 is disposed between the substrate 2 and the light transmissive member 3. The support member 4 is configured to include a resin material, a metal material, or the like.

The support member 4 may be composed of a fluororesin (polytetrafluoroethylene (PTFE)). By causing the support member 4 to be composed of a fluororesin having insulating properties, the ultraviolet light fluid treatment device 100 can reduce the occurrence of electric leakage, electrical noise, and the like even when the support member 4 contacts the substrate 2. Further, the fluororesin has high reflectivity with respect to ultraviolet light. Therefore, by causing the support member 4 to be composed of the fluororesin, the amount of reflected light of the ultraviolet light L, which is reflected by the reflective surface 41, can be increased. Accordingly, the ultraviolet light fluid treatment device 100 can improve the irradiation efficiency of the ultraviolet light L, and thus can improve the treatment efficiency. The upper end of the support member 4 is positioned higher than the light emitting surfaces 11 of the light emitting parts 10. The height of the support member 4 can be, for example, in a range of 0.1 cm to 0.6 cm. The height of the support member 4 is the longest length of the support member 4 in the Z direction.

The reflective surface 41 is positioned between the light source 1 and the adsorption member 5 held by the support member 4, and is configured to reflect the ultraviolet light L from the light source 1 to the light transmissive member 3. For example, the reflective surface 41 reflects the ultraviolet light L, emitted radially from the light emitting surfaces 11 of the plurality of light emitting parts 10, to the light transmissive member 3. The ultraviolet light L reflected by the reflective surface 41 propagates toward the light transmissive member 3, is transmitted through the light transmissive member 3, and is emitted to the fluid 202 in the flow path tube 200.

From the viewpoint of improving the irradiation efficiency of the ultraviolet light L by increasing the amount of reflected light of the ultraviolet light L, which is reflected by the reflective surface 41, the reflective surface 41 is preferably a mirror surface such that light scattering on the reflective surface 41 can be reduced. As used herein, the "mirror surface" means a surface having an arithmetic average roughness Ra of 0.3 μm or less. Further, in order to reduce light absorption on the reflective surface 41, the reflective surface 41 may be covered by a metal film or the like. An aluminum film may be used as the metal film in order to increase the reflectivity of the ultraviolet light L. The film covering the reflective surface 41 may be a single-layer film formed of one material, or may be a multilayer film formed of one or more materials.

The support member 4 is fixed to the substrate 2 by an adhesive member or the like, such that the light source 1 disposed on the substrate 2 is located inside the through hole 42 in a plan view. The through hole 42 allows light emitted from the light source 1 to pass through the through hole 42 toward the light transmissive member 3. In the example illustrated in FIG. 3, the entire inner surface defining the through hole 42 corresponds to the reflective surface 41 described above. The through hole 42 allows light emitted from the light source 1 and reflected by the reflective surface 41 to pass through the through hole 42 toward the light transmissive member 3. The through hole 42 has a substantially circular shape in a plan view. However, the through hole 42 may have a shape other than the substantially circular shape, such as a substantially elliptical shape, a substantially rectangular shape, or a substantially polygonal shape in a plan view.

The recessed portions 43 of the support member 4 are located outside the through hole 42 in a plan view. The support member 4 holds the adsorption member 5 disposed within the recessed portions 43, for example. Each of the recessed portions 43 of the support member 4 can have a depth of 0.05 cm or more and 0.5 cm or less.

The adsorption member 5 includes an adsorbent material adsorbing moisture. The adsorption member 5 is disposed in the vicinity of the light source 1 and the light transmissive member 3 while being held by the support member 4. By disposing the adsorption member 5 in the vicinity of the light source 1, moisture around the light source 1 can be removed. In the present embodiment, the adsorption member 5 may be disposed to overlap the light transmissive member 3 as viewed in the direction normal to the main surface of the light transmissive member 3. With this configuration, the adsorption member 5 can efficiently adsorb moisture condensed on the light transmissive member 3. Thus, the adsorption member 5 can efficiently remove moisture adhering to the light transmissive member 3. Therefore, the ultraviolet light fluid treatment device 100 can suppress a situation in which moisture adhering to the surface of the light transmissive member 3 reflects or refracts the ultraviolet light L from the light source 1 and, as a result, the amount of the ultraviolet light L is decreased. Accordingly, the ultraviolet light fluid treatment device 100 can improve the irradiation efficiency of the ultraviolet light L, and thus can improve the treatment efficiency.

The adsorbent material of the adsorption member 5 may include a porous material composed of at least one material selected from a group consisting of silica gel, activated carbon, and a silicate mineral. With this configuration, the moisture adsorbing efficiency of the adsorption member 5 can be improved, and moisture around the light source 1 can be efficiently removed. The adsorption member 5 may be a powder of the porous material. Examples of the porous material include zeolite.

The adsorption member 5 may be a resin containing the adsorbent material. If the adsorption member 5 is irradiated with the ultraviolet light L from the light source 1, the adsorption member 5 would deteriorate and its ability to adsorb moisture would be decreased. By causing the adsorption member 5 to be composed of a resin containing the adsorbent material, the outer periphery of the adsorption member 5 can be covered by the resin. Therefore, the adsorption member 5 is less likely to be irradiated with the ultraviolet light L, and thus, deterioration of the adsorption member 5 can be suppressed, as compared to when the adsorption member 5 alone that does not include a resin is held by the support member 4. By suppressing deterioration of the adsorption member 5, the adsorption member 5 can efficiently remove moisture around the light source 1.

Further, by causing the adsorption member 5 to be composed of a resin containing the adsorbent material and imparting fluidity to the resin, the resin can be poured into the recessed portions 43, thereby allowing the adsorption member 5 to be spread over the entire support member 4. In this manner, the adsorption member 5 can be held by the support member 4. Accordingly, the time it takes for the support member 4 to hold the adsorption member 5 can be reduced, and thus, the manufacturing efficiency of the ultraviolet light fluid treatment device 100 can be improved. After the adsorption member 5 is poured into the recessed portions 43, the adsorption member 5 can be hardened by being heated, for example. By hardening the adsorption member 5, leakage of the adsorption member 5 from the recessed portions 43 can be reduced. Further, by hardening the adsorption member 5 within the recessed portions 43, the adsorption member 5 is less likely to be scattered and adhere to the light source 1. As a result, deterioration of the light source 1 due to adhesion of the adsorption member 5 to the light source 1 can be suppressed. Accordingly, the ultraviolet light fluid treatment device 100 can reduce a decrease in the treatment efficiency due to the deterioration of the light source 1, and can thus improve the treatment efficiency.

The ultraviolet light fluid treatment device 100 includes the support member 4, and thus, the adsorption member 5 can be disposed integrally with the reflective surface 41 that reflects the ultraviolet light L from the light source 1 to the light transmissive member 3. Therefore, as compared to when the reflective surface 41 and the adsorption member 5 are disposed separately from each other, the size of the ultraviolet light fluid treatment device 100 can be reduced. Accordingly, since moisture around the light source can be efficiently removed as described above, in the present embodiment, the small-sized ultraviolet light fluid treatment device that can efficiently remove moisture around the light source can be provided.

In the present embodiment, an upper end 51 of the adsorption member 5 held by the support member 4 may be positioned lower than an upper end 44 of the support member 4. With this configuration, the ultraviolet light L traveling from the light source 1 toward the adsorption member 5 is blocked by a wall portion 45 located between the light source 1 and the adsorption member 5, and thus, the adsorption member 5 within the recessed portions 43 is less likely to be irradiated with the ultraviolet light L. As a result, deterioration of the adsorption member 5 by being irradiated with ultraviolet light L can be suppressed. Accordingly, moisture around the light source 1 can be efficiently removed.

The upper end 51 of the adsorption member 5 is preferably positioned lower than the upper end 44 of the support member 4 and near the upper end 44 of the support member 4. With this configuration, the adsorption member 5 can be positioned near the light transmissive member 3 disposed above (on the +Z side of) the support member 4, and moisture on the light transmissive member 3 can be efficiently removed. The distance between the upper end 51 of the adsorption member 5 and upper end 44 of the support member 4 can be, for example, in a range of 0.1 to 0.3 mm.

<Example of Detailed Configuration of Light Source 1 and Substrate 2>

Figure 4:
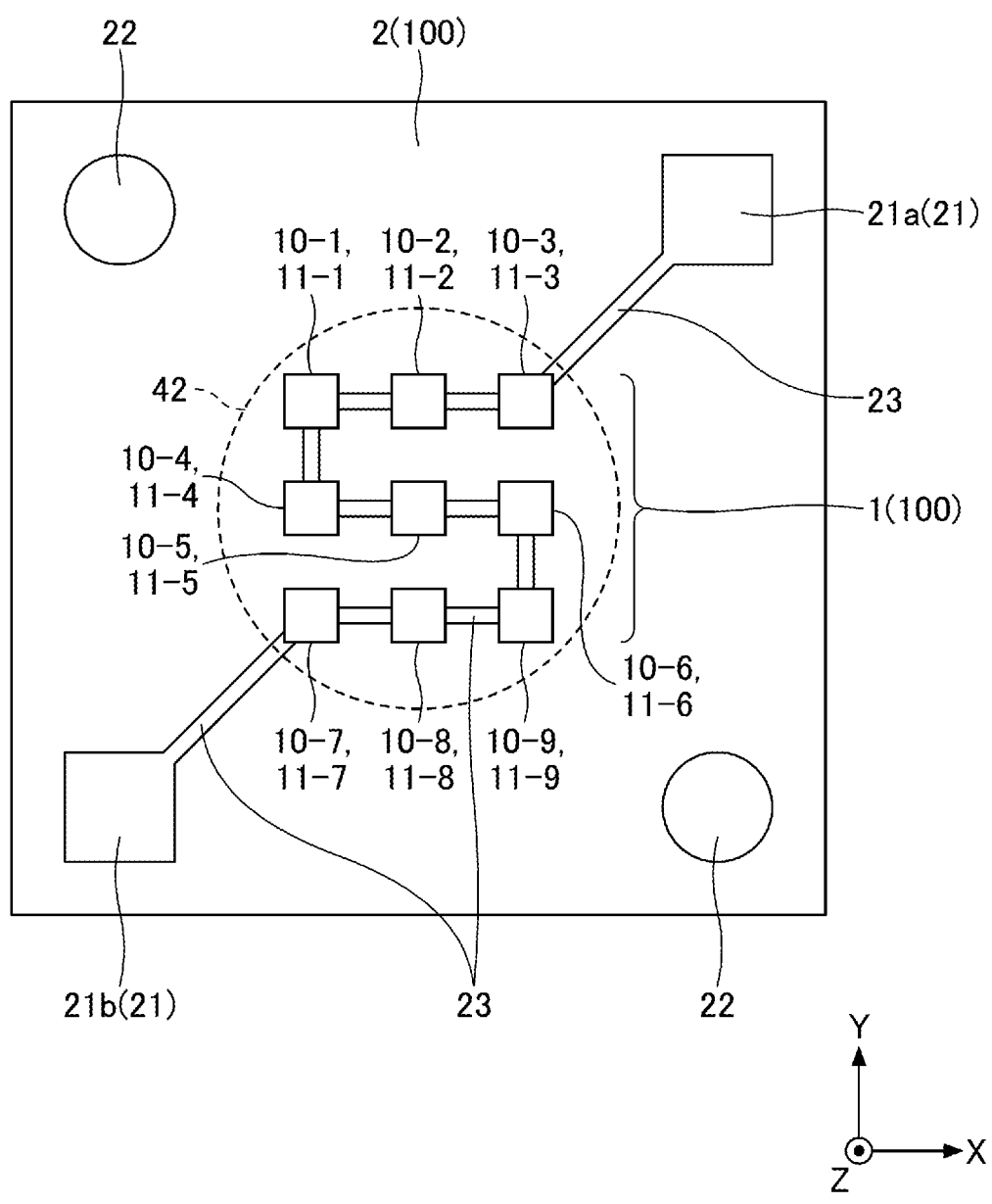
FIG. 4 is a schematic plan view of a substrate on which a light source of FIG. 3 is disposed.

FIG. 4 is a schematic plan view of the substrate 2 on which the light source 1 of FIG. 3 is disposed. As illustrated in FIG. 4, the substrate 2 has a substantially rectangular outer shape in a plan view. However, the substrate 2 may have a shape other than the substantially rectangular shape, such as a substantially elliptical shape, a substantially rectangular shape, or a substantially polygonal shape in a plan view.

Two electrodes 21 and wiring 23 electrically connected to the electrodes 21 are disposed on the surface on the +Z side of the substrate 2. The two electrodes 21 are disposed on one diagonal line of the substrate 2. Two screw holes 22 are disposed on the other diagonal line of the substrate 2. Screw portions configured to be coupled to screw members are formed on the inner surfaces of the screw holes 22. The screw holes 22 are used to fix the support member 4 onto the substrate 2 by coupling the screw portions to the screw members.

As a base material of the substrate 2, an insulating material is preferably used, and a material that does not easily transmit light emitted from the light source 1, external light, or the like is preferably used. Specifically, as the base material of the substrate 2, a ceramic such as alumina, aluminum nitride, mullite, or silicon nitride, or a resin such as a phenol resin, an epoxy resin, a polyimide resin, a bismaleimide triazine (BT) resin, polyphthalamide, or a polyester resin can be used.

In the illustrated example, the light source 1 includes nine light emitting parts 10, that is, light emitting parts 10-1, 10-2, 10-3, 10-4, 10-5, 10-6, 10-7, 10-8, and 10-9. The nine light emitting parts 10-1 through 10-9 are arranged in a matrix. The plurality of light emitting parts 10 are arranged along the X direction, or are arranged along the X direction and the Y direction orthogonal to the X direction. In FIG. 4, the nine light emitting parts 10 are arranged along the X direction and the Y direction.

The nine light emitting parts 10 have nine light emitting surfaces 11. That is, the light emitting part 10-1 has a light emitting surface 11-1, the light emitting part 10-2 has a light emitting surface 11-2, the light emitting part 10-3 has a light emitting surface 11-3, the light emitting part 10-4 has a light emitting surface 11-4, and the light emitting part 10-5 has a light emitting surface 11-5. Further, the light emitting part 10-6 has a light emitting surface 11-6, the light emitting part 10-7 has a light emitting surface 11-7, the light emitting part 10-8 has a light emitting surface 11-8, and the light emitting part 10-9 has a light emitting surface 11-9. The nine light emitting surfaces 11-1 through 11-9 are located inside the through hole 42 of the support member 4 in a plan view. The light emitting parts 10 overlap the light emitting surfaces 11 in a plan view. Therefore, the reference numerals of the light emitting parts 10 and the reference numerals of the light emitting surfaces 11 are illustrated together in FIG. 4.

The light source 1 emits the ultraviolet light L in response to a drive voltage or a drive current supplied from any of the electrodes 21 through the wiring 23. In FIG. 4, a drive voltage or a drive current supplied from an electrode 21a of the two electrodes 21 is supplied through the wiring 23 to the light emitting part 10-3, the light emitting part 10-2, the light emitting part 10-1, the light emitting part 10-4, the light emitting part 10-5, the light emitting part 10-6, the light emitting part 10-9, the light emitting part 10-8, and the light emitting part 10-7 in this order.

The peak wavelength of the ultraviolet light L emitted from the light source 1 is, for example, 10 nm or more and 400 nm or less. The light source 1 includes a light emitting element. As the light emitting element, a light emitting diode (LED) or a laser diode (LD) can be used, for example. The light source 1 can use a light emitting device in which a light emitting element is mounted on a substrate 2, a light emitting device in which a housing including a light emitting element is mounted on a substrate 2, or the like.

The number of light emitting parts 10 included in the light source 1 is not limited to nine, and can be appropriately changed according to the type or the like of a fluid to be treated. The arrangements of the light emitting parts 10, the electrode 21, and the screw holes 22 are not limited to those illustrated in FIG. 4, and can be appropriately changed according to the shape or the like of the support member 4.

<Example of Detailed Configuration of Support Member 4>

Figure 5:
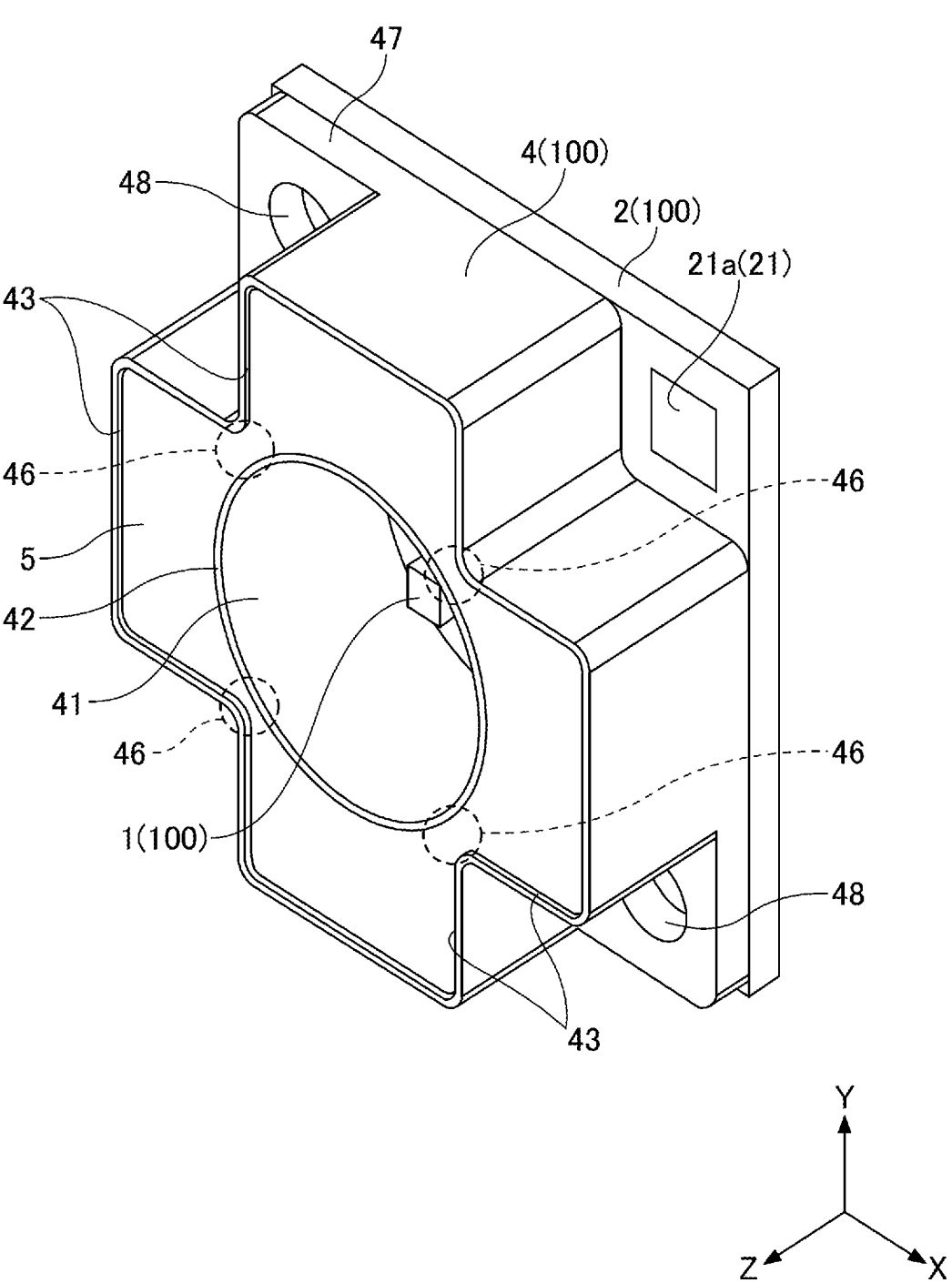
FIG. 5 is a schematic perspective view of a support member fixed to the substrate of FIG. 3.
Figure 6:
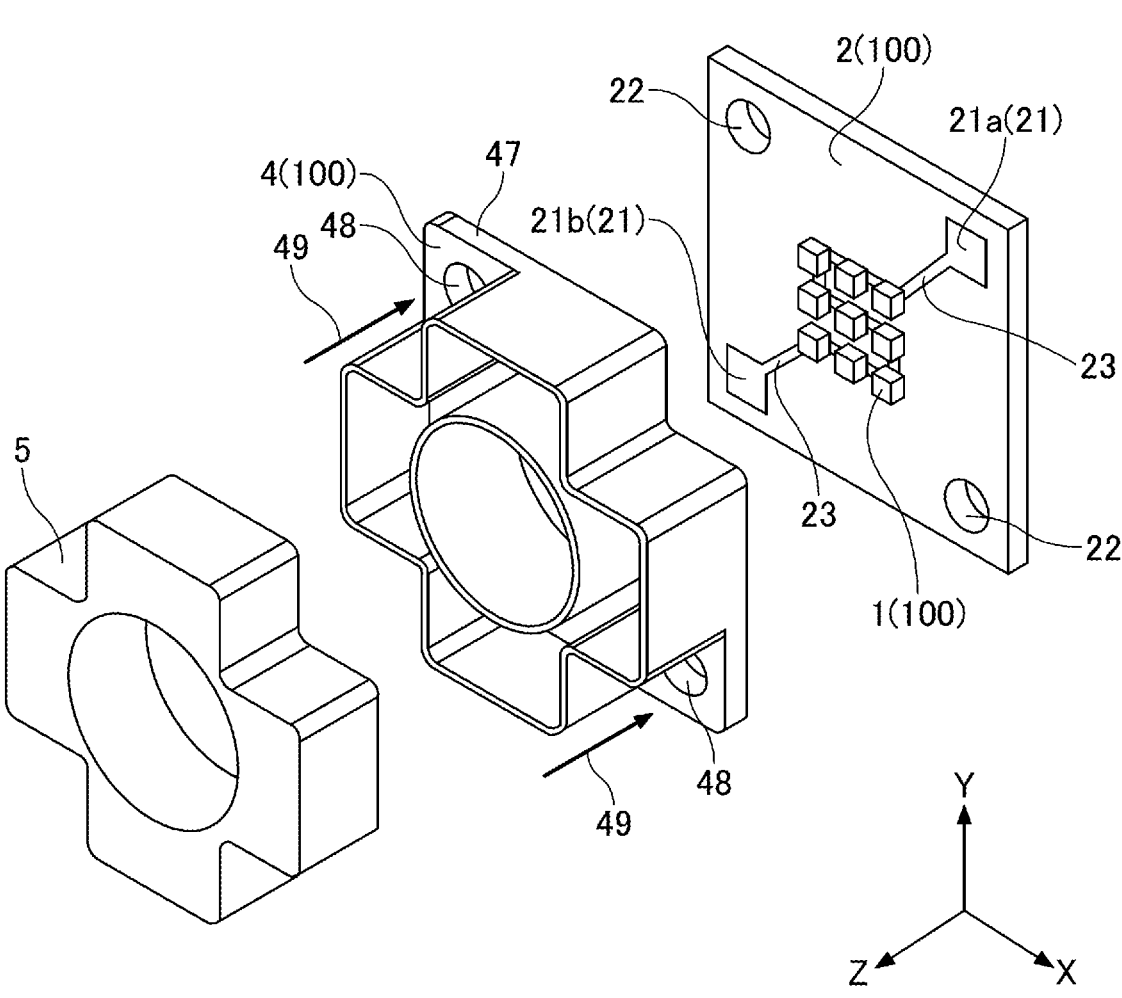
FIG. 6 is a schematic exploded perspective view of the support member and the substrate of FIG. 5.

The detailed configuration of the support member 4 will described with reference to FIG. 5 and FIG. 6. FIG. 5 is a schematic perspective view of the support member 4 fixed to the substrate 2 of FIG. 3. FIG. 6 is a schematic exploded perspective view of the support member 4 and the substrate 2 of FIG. 5.

As illustrated in FIG. 5, in the present embodiment, the reflective surface 41 of the support member 4 may be disposed around the light source 1, and the adsorption member 5 may be disposed around the reflective surface 41. In the example illustrated in FIG. 5, the recessed portions 43 are disposed on the +Y side, the −Y side, the +X side, and the −X side, and the adsorption member 5 is held mainly by these four recessed portions 43. With this configuration, the ultraviolet light fluid treatment device 100 can cause the ultraviolet light from the light source 1 to be reflected by the reflective surface 41, and thus, the adsorption member 5 is less likely to be directly irradiated with the ultraviolet light. Further, in the ultraviolet light fluid treatment device 100, the adsorption member 5 can be easily disposed near the light transmissive member 3 so as to overlap the light transmissive member 3 over a wide range. Accordingly, moisture condensed on the light transmissive member 3 can be efficiently removed.

As illustrated in FIG. 5, in the present embodiment, the adsorption member 5 may be continuously disposed around the reflective surface 41. Specifically, adjacent recessed portions 43, of the four recessed portions 43 disposed on the +Y side, the −Y side, the +X side, and the −X side of the reflective surface 41, are not separated and may be continuous to each other through a connection portion 46. With this configuration, the area in which the adsorption member 5 is disposed around the light source 1 can be increased by the area of the connection portion 46, as compared to when adsorption members separated from one another are disposed around the light source 1. As a result, the ultraviolet light fluid treatment device 100 can improve the adsorbing efficiency of the adsorption member 5 with respect to moisture condensed on the light transmissive member 3.

Further, with the above-described configuration, when the adsorption member 5 composed of a fluid resin is poured into the recessed portions 43 such that the adsorption member 5 can be held within the recessed portions 43, the adsorption member 5 can be spread over the entire recessed portions 43 through connection portions 46 without changing the position where the fluid resin is poured. Accordingly, the time it takes for the support member 4 to hold the adsorption member 5 can be reduced, as compared to when the fluid resin is poured into multiple recessed portions 43 that are separated from one another and disposed around the light source 1. Therefore, the manufacturing efficiency of the ultraviolet light fluid treatment device 100 can be enhanced.

As illustrated in FIG. 5, the support member 4 may have a shape that allows the electrodes 21 not to overlap the support member 4 when the support member 4 is fixed to the substrate 2. When the support member 4 has such a shape, the electrodes 21 can be exposed in a state in which the support member 4 is fixed to the substrate 2, and a drive voltage or a drive current can be easily supplied. In addition, the support member 4 can be formed in a shape in which portions of the support member 4, facing the electrodes 21 in a state in which the support member 4 is fixed to the substrate 2, are removed. Therefore, the electrodes 21 can be exposed while the size of the ultraviolet light fluid treatment device 100 can be reduced.

As illustrated in FIG. 5 and FIG. 6, in the present embodiment, the support member 4 may have attachment holes 48 at positions that are inward of an outer edge 47 of the support member 4 and that do not overlap the adsorption member 5 in a plan view. The support member 4 is fixed to the substrate 2 by fixing members 49 inserted into the attachment holes 48. In FIG. 6, the adsorption member 5 that is hardened by being heated or the like is depicted.

The fixing members 49 are, for example, screw members. In FIG. 6, the illustration of the fixing members 49 are simplified by using arrows that indicate the direction in which the fixing members 49, which are the screw members, are inserted. The fixing members 49 are inserted into the attachment holes 48 and coupled to the screw holes 22 of the substrate 2, thereby fixing the support member 4 to the substrate 2. With this configuration, the attachment holes 48 can be provided at positions near the center of the support member 4, and thus, the size of the ultraviolet light fluid treatment device 100 can be reduced as compared to when the attachment holes 48 are provided outward of the outer edge 47 of the support member 4.

According to the present disclosure, a small-sized ultraviolet light fluid treatment device that can adsorb moisture around a light source can be provided.

The embodiments of the present disclosure have been described above with reference to specific examples. However, the present disclosure is not limited to these examples. All embodiments that can be implemented by a person skilled in the art modifying the above described embodiments of the present disclosure are encompassed by the scope of the present disclosure as long as the gist of the present disclosure is encompassed. In addition, within the scope of the spirit of the present disclosure, a person skilled in the art can conceive various changes and modifications, and it is understood that the changes and modifications fall within the scope of the present disclosure.

What is claimed is:

1. An ultraviolet light fluid treatment device for irradiating a fluid flowing in a flow path tube with ultraviolet light, the ultraviolet light fluid treatment device comprising:

a substrate;

a light source disposed on the substrate and configured to emit the ultraviolet light;

a light transmissive member disposed between the light source and the flow path tube and configured to transmit the ultraviolet light from the light source; and a support member fixed to the substrate and configured to hold an adsorption member that includes an adsorbent material adsorbing moisture, wherein the support member includes:

a through hole inside of which the light source is disposed in a plan view as seen in a direction normal to a main surface of the light transmissive member;

a recessed portion which is located outside the through hole in the plan view and is open towards the light transmissive member; and a wall portion partitioning the through hole and the recessed portion, wherein an inner surface of the wall portion defining the through hole is a reflective surface, and the adsorption member is disposed within the recessed portion such that the wall portion is located between the light source and the adsorption member.

2. The ultraviolet light fluid treatment device according to claim 1, wherein an upper end of the adsorption member is positioned lower than an upper end of the support member.

3. The ultraviolet light fluid treatment device according to claim 1, wherein the adsorption member overlaps the light transmissive member as viewed in a direction normal to a main surface of the light transmissive member.

4. The ultraviolet light fluid treatment device according to claim 2, wherein the adsorption member overlaps the light transmissive member as viewed in a direction normal to a main surface of the light transmissive member.

5. The ultraviolet light fluid treatment device according to claim 1, wherein the reflective surface is disposed around the light source, and the adsorption member is disposed around the reflective surface.

6. The ultraviolet light fluid treatment device according to claim 2, wherein the reflective surface is disposed around the light source, and the adsorption member is disposed around the reflective surface.

7. The ultraviolet light fluid treatment device according to claim 3, wherein the reflective surface is disposed around the light source, and the adsorption member is disposed around the reflective surface.

8. The ultraviolet light fluid treatment device according to claim 5, wherein the adsorption member is continuously disposed around the reflective surface.

9. The ultraviolet light fluid treatment device according to claim 6, wherein the adsorption member is continuously disposed around the reflective surface.

10. The ultraviolet light fluid treatment device according to claim 7, wherein the adsorption member is continuously disposed around the reflective surface.

11. The ultraviolet light fluid treatment device according to claim 1, wherein the support member has an attachment hole at a position that is inward of an outer edge of the support member and that does not overlap the adsorption member as viewed in a direction normal to a main surface of the light transmissive member, and the support member is fixed to the substrate by a fixing member inserted into the attachment hole.

12. The ultraviolet light fluid treatment device according to claim 2, wherein the support member has an attachment hole at a position that is inward of an outer edge of the support member and that does not overlap the adsorption member as viewed in a direction normal to a main surface of the light transmissive member, and the support member is fixed to the substrate by a fixing member inserted into the attachment hole.

13. The ultraviolet light fluid treatment device according to claim 3, wherein the support member has an attachment hole at a position that is inward of an outer edge of the support member and that does not overlap the adsorption member as viewed in a direction normal to a main surface of the light transmissive member, and the support member is fixed to the substrate by a fixing member inserted into the attachment hole.

14. The ultraviolet light fluid treatment device according to claim 1, wherein the adsorption member comprises a resin containing the adsorbent material.

15. The ultraviolet light fluid treatment device according to claim 2, wherein the adsorption member comprises a resin containing the adsorbent material.

16. The ultraviolet light fluid treatment device according to claim 3, wherein the adsorption member comprises a resin containing the adsorbent material.

17. The ultraviolet light fluid treatment device according to claim 1, wherein the adsorbent material comprises a porous material comprising at least one material selected from a group consisting of silica gel, activated carbon, and a silicate mineral.

18. The ultraviolet light fluid treatment device according to claim 2, wherein the adsorbent material comprises a porous material comprising at least one material selected from a group consisting of silica gel, activated carbon, and a silicate mineral.

19. The ultraviolet light fluid treatment device according to claim 3, wherein the adsorbent material comprises a porous material comprising at least one material selected from a group consisting of silica gel, activated carbon, and a silicate mineral.

* * * * *